United States Patent [19]

Ertl et al.

[11] Patent Number: 4,797,436

[45] Date of Patent: Jan. 10, 1989

[54] OLIGOMERIC DIAZAOXASPIRODECANES, PREPARATION THEREOF AND USE THEREOF AS LIGHT STABILIZERS FOR POLYMERS

[75] Inventors: Josef Ertl, Wertingen; Helmut Korbanka, Adelsried, both of Fed. Rep. of Germany

[73] Assignee: Hoechst Aktiengesellschaft, Frankfurt am Main, Fed. Rep. of Germany

[21] Appl. No.: 934,109

[22] Filed: Nov. 24, 1986

[30] Foreign Application Priority Data

Nov. 26, 1985 [DE] Fed. Rep. of Germany ....... 3541664

[51] Int. Cl.$^4$ .................... C08K 5/34; C07D 498/10
[52] U.S. Cl. ........................... 524/97; 546/19
[58] Field of Search ............ 546/18, 19, 20; 524/95, 524/96, 97

[56] References Cited

U.S. PATENT DOCUMENTS 4,405,735 9/1983 Wiezer et al. .................... 524/95

FOREIGN PATENT DOCUMENTS 2606026 8/1977 Fed. Rep. of Germany .
2634957 2/1978 Fed. Rep. of Germany .
2941004 4/1981 Fed. Rep. of Germany .
3104294 8/1982 Fed. Rep. of Germany .

Primary Examiner—Kriellion Morgan

[57] ABSTRACT

The present invention relates to oligomeric tetraalkylpiperidine light stabilizers for polymers, to the preparation thereof from known polyalkyldiazaspirodecanes and epoxides, and to the use thereof for stabilizing polymers against the damaging effect of light, heat and oxygen.

12 Claims, No Drawings

OLIGOMERIC DIAZAOXASPIRODECANES, PREPARATION THEREOF AND USE THEREOF AS LIGHT STABILIZERS FOR POLYMERS

The present invention relates to novel, sterically hindered amine light stabilizers, to the preparation thereof and to the use thereof for stabilizing synthetic polymers to the action of light, heat and oxygen.

It is known to react polyalkyldiazaspirodecanes with epichlorohydrin to give the corresponding polyethers (cf. German Offenlegungsschrift No. 2,941,004).

Also known are reactions of diazaoxaspirodecanes with epoxides (cf. German Offenlegungsschrift No. 3,104,294).

The present invention, then, relates to compounds of the formula (I)

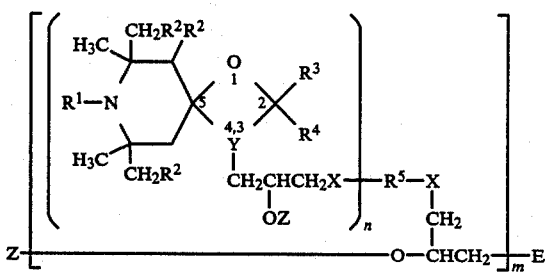

in which
n is a whole number from 1 to 4, preferably 1,
m is a whole number from 1 to 100, preferably 1 to 20, in particular 2 to 20,
$R^1$ is hydrogen, $C_1$- to $C_4$-alkyl, benzyl, allyl, $C_2$- to $C_{30}$-alkanoyl, $C_2$- to $C_{20}$-alkenoyl, $C_7$- to $C_{11}$-aroyl, $C_8$- to $C_{14}$-arylalkanoyl or $C_8$- to $C_{20}$-alkylaryl, preferably hydrogen, $C_1$- to $C_4$-alkyl, $C_2$- to $C_{30}$-alkanoyl, in particular hydrogen or acyl, very particularly preferably hydrogen,
$R^2$ is hydrogen or $C_1$- to $C_4$-alkyl, preferably hydrogen,
$R^3$ and $R^4$ are identical or different and denote hydrogen, $C_1$- to $C_{13}$-alkyl, preferably $C_1$- to $C_9$-alkyl, unsubstituted or chlorine- or $C_1$- to $C_4$-alkyl-substituted phenyl, unsubstituted or $C_1$- to $C_4$-alkyl-substituted $C_7$- to $C_{14}$-aralkyl, preferably $C_7$- to $C_9$-phenylalkyl, or together with the carbon atom connecting them denote an unsubstituted or $C_1$- to $C_4$-alkyl-mono-, -di-, -tri- or -tetra-substituted $C_5$- to $C_{12}$-cycloalkyl or piperidine ring,
$R^5$ when n=1 denotes $C_2$- to $C_{18}$-alkylene, preferably $C_2$- to $C_{12}$-alkylene, unsubstituted or $C_1$- to $C_4$, preferably $C_1$-alkyl-, mono- or -di-substituted phenylene, α,ω-dicarboxy-$C_1$- to $C_8$-alkylene, a dicarboxy-$C_6$-ring, $C_7$- to $C_{14}$-aralkylene, cycloalkylene, dicycloalkylene, tricycloalkylene, bismethylenemonocycloalkylene, bismethylenedicycloalkylene, bismethylenetricycloalkylene, arylene, bisarylenealkyl, which radicals can also be bromine-or chlorine- or $C_1$–$C_4$-alkyl-substituted, a radical

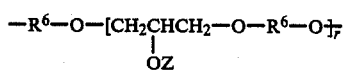

with r=1 to 20 and $R^6$ equal to $C_2$- to $C_{12}$-alkylene, cycloalkylene, dicycloalkylene, tricycloalkylene, bismethylenemonocycloalkylene, bismethylenedicycloalkylene, arylene, bisarylenealkyl, which radicals can also be bromine- or chlorine- or $C_1$- to $C_4$-alkyl-substituted, $R^5$ when n=2 denotes the radical of a trifunctional alcohol or amine, the trifunctional radical of an aliphatic alcohol which contains further hydroxyl groups, or the trifunctional radical of a novolak based on phenol, cresol, bisphenol-F or bisphenol-A, $R^5$ when n=3 denotes the tetrafunctional radical of an aliphatic alcohol or amine, preferably the pentaerythrityl radical, or of a novolak based on phenol, cresol, bisphenol-F or bisphenol-A or the radical

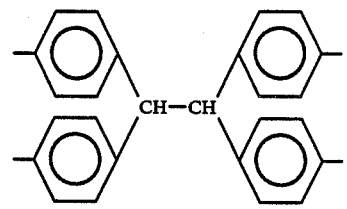

$R^5$ when n=4 denotes a pentafunctional radical of a polyol, or a polyamine or of a novolak based on phenol, cresol, bisphenol-F or bisphenol-A,
Y denotes

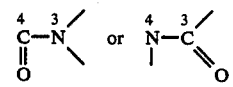

and occupies ring positions 3, 4 in the formula I,
X represents —O— or

where $R^7$ is hydrogen, $C_1$- to $C_{30}$-alkyl, a piperidine ring which is substituted by 1 to 4 $C_1$- to $C_4$-alkyl groups, or a radical of the formula (II)

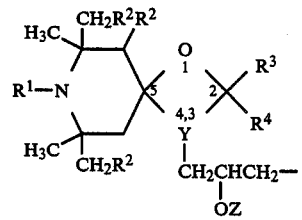

in which $R^1$, $R^2$, $R^3$, $R^4$, Y have the abovementioned meanings,
Z is hydrogen,
E stands for hydrogen, hydroxyl, a radical of the formula (IV), (V) or (VI)

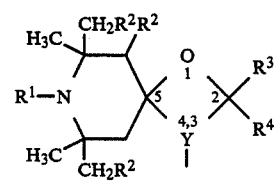

-continued

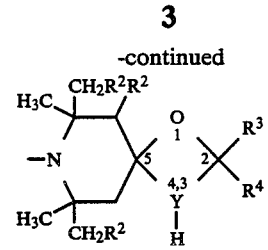
(V)

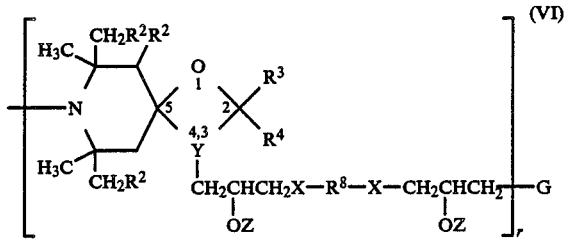
(VI)

in which R¹, R², R³, R⁴, R⁵, X, Y and Z have the abovementioned meanings, r represents a whole number from 1 to 100, preferably 1 to 20, and G is a radical of the formula (IV) or (V) and R⁸ has the meaning of formula (VII)

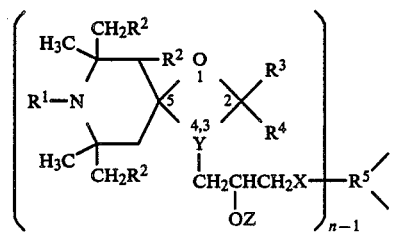
(VII)

in which R¹, R², R³, R⁴, R⁵, X, Y, Z and n have the abovementioned meanings.

These novel light stabilizers of the formula I are prepared from diazaspirodecanes of the formula (VIIIa) or (VIIIb)

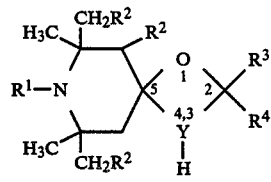
(VIIIa)

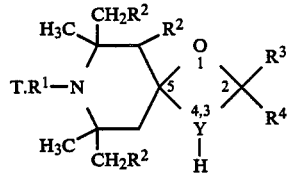
(VIIIb)

in which R¹, R², R³, R⁴ and Y have the abovementioned meanings and T is a nonoxidizing mineral acid or an aliphatic or aromatic sulfonic or phosphonic acid, an aliphatic mono-, di- or poly-carboxylic acid or an aromatic mono- or di-carboxylic acid, and epoxides of the formula (IXa) or (IXb)

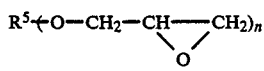
(IXa)

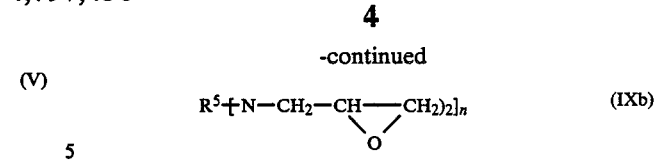
(IXb)

in which R⁵ and n have the abovementioned meanings, the compounds of the formula (VIII) being used in a deficiency of one to one fifth of an equivalent, based on the epoxy groups in the formulae (IXa) or (IXb). This reaction takes place in an inert organic solvent, for example toluene or xylene, in the presence of 0.1 to 1.5 times the equivalent amount of base, relative to the compound (VIIIa), or 1.2 to 2.5 times the equivalent amount of a base in the case of using the compounds (VIIIb), preferably with 0.3 to 1.2 times or 1.3 to 2.2 times the equivalent amount of sodium hydroxide or potassium hydroxide respectively, a phase transfer catalyst being added if desired. The reaction temperature is 40° to 180° C., preferably 50° to 150° C., particularly preferably 80° to 110° C.

The intermediates obtained in this reaction step still contain epoxy groups, so that these intermediates can be converted in the presence or absence of a solvent, and if desired in the absence of catalysts, into higher molecular weight compounds. This can be effected for example by heating these intermediates to 100° to 240° C., preferably 140° to 210° C., in particular 160° to 200° C. Herein it is also possible to add salts as catalysts, basic compounds such as, for example, BaCO₃ favoring polyether formation, while acid compounds, such as, for example, NH₄Cl, favor the addition of the amine function onto the epoxy group.

To prepare the polymers or oligomers, it is also possible to proceed by not first isolating the epoxy-containing intermediates, but bringing them in the reaction mixture to the higher temperatures mentioned and working up after polymerization or polyaddition has taken place.

The degrees of polymerization/polyaddition can be affected not only by the ratio of the starting materials to one another but also by the reaction conditions. For instance, increasing the content of epoxy compounds IX relative to the diazaspirodecanes VIII leads to higher average molecular weights. Similarly, prolonging the polymerization/polyaddition times and increasing the polymerization/polyaddition temperature leads to higher molecular weight products.

In the formation of higher molecular weight products, the reactions which take place here can in principle be as follows:
polyether formation from the epoxy groups (polymerization),
addition of the amine function onto the epoxy groups (polyaddition) and/or
addition of existing hydroxyl groups onto the epoxy groups (polyaddition).

Surprisingly, the above-described reaction management permits the preparation of compounds having a certain average molecular weight, it being possible to vary the latter in a controlled manner within wide limits.

Compared with the compounds of German Offenlegungsschrift No. 3,104,294, the big advantage is that, in the case of the compounds according to the invention, there is no need to use epichlorohydrin, a substance which in animal experiments has been clearly found to be carcinogenic.

The starting materials of the formula (VIIIa) or (VIIIb) are already good stabilizers in themselves, but are not satisfactory in particular in respect of the compatibility with the polymer to be stabilized and in respect of volatility. The stabilizers according to the invention do not have these disadvantages and surprisingly also have a distinctly better antioxidative and light-stabilizing action.

Suitable compounds for the formula VIIIa are for example:

1. 2-Butyl-7,7,9,9,-tetramethyl-1-oxa-3,8-diaza-4-oxo-spiro-[4.5]-decane
2. 2-iso-Butyl-7,7,9,9,-tetramethyl-1-oxa-3,8-diaza-4-oxo-spiro-[4.5]-decane
3. 2-Pentyl-7,7,9,9,-tetramethyl-1-oxa-3,8-diaza-4-oxo-spiro-[4.5]-decane
4. 2-iso-Pentyl-7,7,9,9,-tetramethyl-1-oxa-3,8-diaza-4-oxa-spiro-[4.5]-decane
5. 2-Hexyl-7,7,9,9,-tetramethyl-1-oxa-3,8-diaza-4-oxa-spiro-[4.5]-decane
6. 2-Heptyl-7,7,9,9,-tetramethyl-1-oxa-3,8-diaza-4-oxo-spiro-[4.5]-decane
7. 2-iso-Heptyl-7,7,9,9,-tetramethyl-1-oxa-3,8-diaza-4-oxo-spiro-[4.5]-decane
8. 2-Nonyl-7,7,9,9,-tetramethyl-1-oxa-3,8-diaza-4-oxo-spiro-[4.5]-decane
9. 2-iso-Nonyl-7,7,9,9,-tetramethyl-1-oxa-3,8-diaza-4-oxo-spiro-[4.5]-decane
10. 2-Undecyl-7,7,9,9,-tetramethyl-1-oxa-3,8-diaza-4-oxo-spiro-[4.5]-decane
11. 2-Phenyl-7,7,9,9,-tetramethyl-1-oxa-3,8-diaza-4-oxo-spiro-[4.5]-decane
12. 2-(4-Chloro-phenyl)-7,7,9,9,-tetramethyl-1-oxa-3,8-diaza-4-oxo-spiro-[4.5]-decane
13. 2-Ethyl-2,7,7,9,9,-pentamethyl-1-oxa-3,8-diaza-4-oxo-spiro-[4.5]-decane
14. 2-Propyl-2,7,7,9,9,-pentamethyl-1-oxa-3,8-diaza-4-oxo-spiro-[4.5]-decane
15. 2-iso-Propyl-2,7,7,9,9,-pentamethyl-1-oxa-3,8-diaza-4-oxo-spiro-[4.5]-decane
16. 2-Butyl-2,7,7,9,9,-pentamethyl-1-oxa-3,8-diaza-4-oxo-spiro-[4.5]-decane
17. 2-iso-Butyl-2,7,7,9,9,-pentamethyl-1-oxo-3,8-diaza-4-oxo-spiro-[4.5]-decane
18. 2-Pentyl-2,7,7,9,9,-pentamethyl-1-oxa-3,8-diaza-4-oxo-spiro-[4.5]-decane
19. 2-Hexyl-2,7,7,9,9,-pentamethyl-1-oxa-3,8-diaza-4-oxo-spiro-[4.5]-decane
20. 2-Nonyl-2,7,7,9,9,-pentamethyl-1-oxa-3,8-diaza-4-oxo-spiro-[4.5]-decane
21. 2,2,7,7,9,9,-Hexamethyl-1-oxa-3,8-diaza-4-oxo-spiro-[4.5]-decane
22. 2,2,7,7,8,9,9,-Heptamethyl-1-oxa-3,8-diaza-4-oxo-spiro-[4.5]-decane
23. 2,2-Diethyl-7,7,9,9,-tetramethyl-1-oxa-3,8-diaza-4-oxo-spiro-[4.5]-decane
24. 2,2-Dipropyl-7,7,9,9,-tetramethyl-1-oxa-3,8-diaza-4-oxo-spiro-[4.5]-decane
25. 2,2-Dibutyl-7,7,9,9,-tetramethyl-1-oxa-3,8-diaza-4-oxo-spiro-[4.5]-decane
26. 2-Ethyl-2-pentyl-7,7,9,9,-tetramethyl-1-oxa-3,8-diaza-4-oxo-spiro-[4.5]-decane
27. 2,2-Dibenzyl-7,7,9,9,-tetramethyl-1-oxa-3,8-diaza-4-oxo-spiro-[4.5]-decane
28. 2,2,4,4-Tetramethyl-7-oxa-3,13-diaza-14-oxo-dispiro-[5.1.4.2]-tetradecane
29. 2,2,4,4-Tetramethyl-7-oxa-3,14-diaza-15-oxo-dispiro-[5.1.5.2]-pentadecane
30. 2,2,4,4-Tetramethyl-7-oxa-3,20-diaza-21-oxo-dispiro-[5.1.11.2]-heneicosane
31. 2,2,7,7,9,9-Hexamethyl-1-oxa-3,8-diaza-4-oxo-8-acetyl-spiro-[4.5]-decane
32. 2,2,4,4-Tetramethyl-7-oxa-3,14-diaza-15-oxo-3-acetyl-dispiro-[5.1.5.2]-pentadecane
33. 2,2,4,4-Tetramethyl-7-oxa-3,20-diaza-21-oxo-3-acetyl-dispiro-[5.1.11.2]-heneicosane
34. 2,7,7,9,9-Pentamethyl-1-oxa-4.8-diaza-3-oxo-spiro-[4.5]-decane
35. 2-Ethyl-7,7,9,9-tetramethyl-1-oxa-4,8-diaza-3-oxo-spiro-[4.5]-decane
36. 2-Propyl-7,7,9,9-tetramethyl-1-oxa-4,8-diaza-3-oxo-spiro-[4.5]-decane
37. 2-Butyl-7,7,9,9-tetramethyl-1-oxa-4,8-diaza-3-oxo-spiro-[4.5]-decane
38. 2-iso-Butyl-7,7,9,9-tetramethyl-1-oxa-4,8-diaza-3-oxo-spiro-[4.5]-decane
39. 2-Pentyl-7,7,9,9-tetramethyl-1-oxa-4,8-diaza-3-oxo-spiro-[4.5]-decane
40. 2-iso-Pentyl-7,7,9,9-tetramethyl-1-oxa-4,8-diaza-3-oxo-spiro-[4.5]-decane
41. 2-iso-Heptyl-7,7,9,9-tetramethyl-1-oxa-4,8-diaza-3-oxo-spiro-[4.5]-decane
42. 2-Phenyl-7,7,9,9-tetramethyl-1-oxa-4,8-diaza-3-oxo-spiro-[4.5]-decane
43. 2,2,7,7,9,9-Hexamethyl-1-oxa-4,8-diaza-3-oxo-spiro-[4.5]-decane
44. 2,2,7,7,8,9,9-Heptamethyl-1-oxa-4,8-diaza-3-oxo-spiro-[4.5]-decane
45. 2,2-Diethyl-7,7,9,9-tetramethyl-1-oxa-4,8-diaza-3-oxo-spiro-[4.5]-decane 46. 2,2-Diethyl-7,7,8,9,9-pentamethyl-1-oxa-4,8-diaza-3-oxo-spiro-[4.5]-decane
47. 2,2-Dipropyl-7,7,9,9-tetramethyl-1-oxa-4,8-diaza-3-oxo-spiro-[4.5]-decane
48. 2,2-Dibutyl-7,7,9,9-tetramethyl-1-oxa-4,8-diaza-3-oxo-spiro-[4.5]-decane
49. 2,2-Dipentyl-7,7,9,9-tetramethyl-1-oxa-4,8-diaza-3-oxo-spiro-[4.5]-decane
50. 2-Ethyl-2,7,7,9,9-pentamethyl-1-oxa-4,8-diaza-3-oxo-spiro-[4.5]-decane
51. 2-Propyl-2,7,7,9,9-pentamethyl-1-oxa-4,8-diaza-3-oxo-spiro-[4.5]-decane
52. 2-iso-Propyl-2,7,7,9,9-pentamethyl-1-oxa-4,8-diaza-3-oxo-spiro-[4.5]-decane
53. 2-Butyl-2,7,7,9,9-pentamethyl-1-oxa-4,8-diaza-3-oxo-spiro-[4.5]-decane
54. 2-iso-Butyl-2,7,7,9,9-pentamethyl-1-oxa-4,8-diaza-3-oxo-spiro-[4.5]-decane
55. 2-Pentyl-2,7,7,9,9-pentamethyl-1-oxa-4,8-diaza-3-oxo-spiro-[4.5]-decane
56. 2-iso-Pentyl-2,7,7,9,9-pentamethyl-1-oxa-4,8-diaza-3-oxo-spiro-[4.5]-decane
57. 2-Hexyl-2,7,7,9,9-pentamethyl-1-oxa-4,8-diaza-3-oxo-spiro-[4.5]-decane
58. 2-Heptyl-2,7,7,9,9-pentamethyl-1-oxa-4,8-diaza-3-oxo-spiro-[4.5]-decane
59. 2-Nonyl-2,7,7,9,9-pentamethyl-1-oxa-4,8-diaza-3-oxo-spiro-[4.5]-decane
60. 2-Undecyl-2,7,7,9,9-pentamethyl-1-oxa-4,8-diaza-3-oxo-spiro-[4.5]-decane
61. 2-Ethyl-2-butyl-7,7,9,9-tetramethyl-1-oxa-4,8-diaza-3-oxo-spiro-[4.5]-decane
62. 2-Ethyl-2-pentyl-7,7,9,9-tetramethyl-1-oxa-4,8-diaza-3-oxo-spiro-[4.5]-decane
63. 2-Ethyl-2-iso-pentyl-7,7,9,9-tetramethyl-1-oxa-4,8-diaza-spiro-[4.5]-decane 64. 2,2,7,7,9,9-Hexamethyl-1-oxa-4,8-diaza-3-oxo-8-acetyl-spiro-[4.5]-decane
65. 2,2-Diethyl-7,7,9,9-tetramethyl-1-oxa-4,8-diaza-3-oxo-8-acetyl-spiro-[4.5]-decane
66. 2,2,4,4-Tetramethyl-7-oxa-3,14-diaza-13-oxo-dispiro-[5.1.4.2]-tetradecane
67. 2,2,4,4-Tetramethyl-7-oxa-3,15-diaza-14-oxo-dispiro-[5.1.5.2]-pentadecane
68. 2,2,4,4-Tetramethyl-7-oxa-3,21-diaza-20-oxo-dispiro-[5.1.11.12]-heneicosane Suitable compounds of the formula VIIIb are the salts of the compounds of the formula VIIIa with protonic acids, for example hydrogen chloride, sulfuric acid, phosphoric acid and the like, for example the hydrochlorides of the above-indicated compounds No. 1–68. The following examples may be mentioned by way of illustration:

69. 2,2,7,7,9,9-Hexamethyl-1-oxa-3,8-diaza-4-oxo-spiro-[4.5]-decane hydrochloride
70. 2,2,4,4-Tetramethyl-7-oxa-3,14-diaza-15-oxo-dispiro-[5.1.5.2]-pentadecane hydrochloride
71. 2,2,4,4-Tetramethyl-7-oxa-3,20-diaza-21-oxo-dispiro-[5.1.11.2]-heneicosane hydrochloride
72. 2,2,7,7,9,9-Hexamethyl-1-oxa-4,8-diaza-3-oxo-spiro-[4.5]-decane hydrochloride
73. 2,2-Diethyl-7,7,9,9-tetramethyl-1-oxa-4,8-diaza-3-oxo-spiro-[4.5]-decane hydrochloride
74. 2,2,4,4-Tetramethyl-7-oxa-3,14-diaza-13-oxo-dispiro-[5.1.4.2]-tetradecane hydrochloride
75. 2,2,4,4-Tetramethyl-7-oxa-3,15-diaza-14-oxo-dispiro-[5.1.5.2]-pentadecane hydrochloride
76. 2,2,4,4-Tetramethyl-7-oxa-3,21-diaza-20-oxo-dispiro-[5.1.11.2]-heneicosane hydrochloride Examples of the epoxides of the formula IX are:

77.

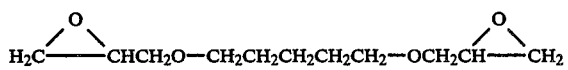
78.

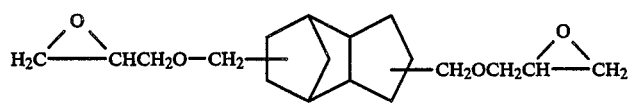
79.

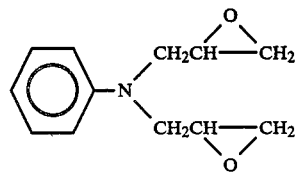
80.

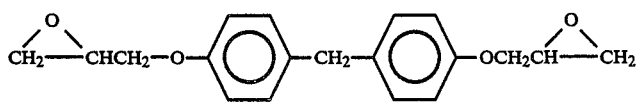
81.

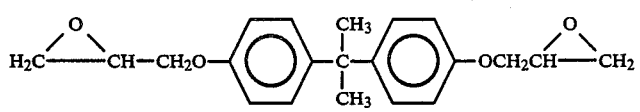
82.

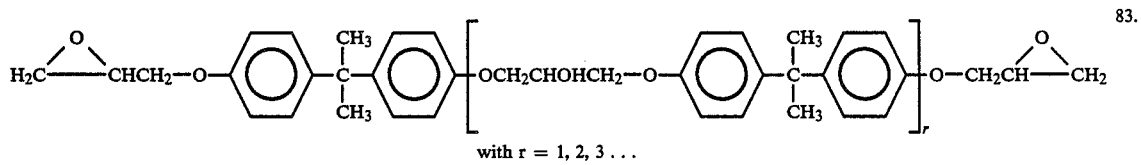
83.

with r = 1, 2, 3 . . .

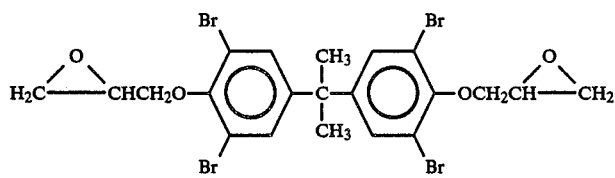
84.

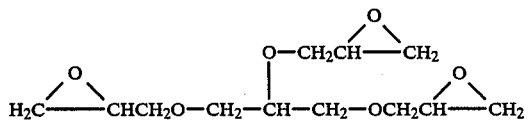
85.

-continued

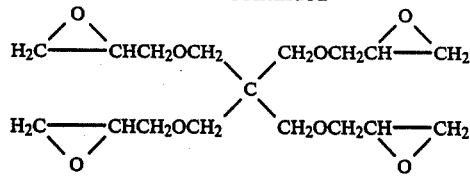

86.

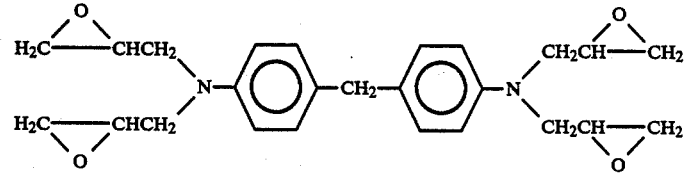

87.

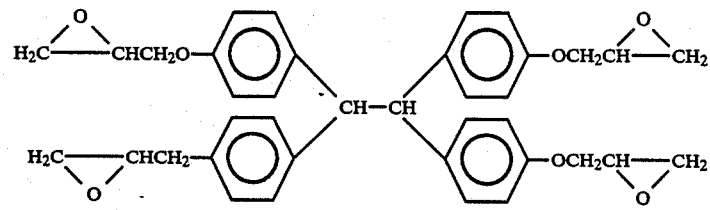

88.

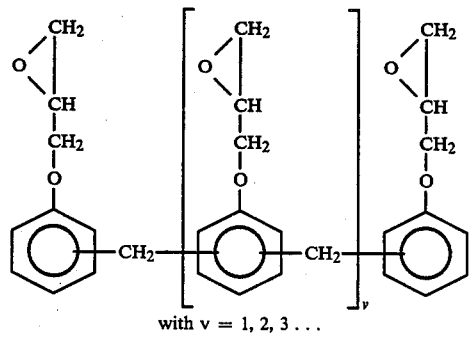

with v = 1, 2, 3 ...

89.

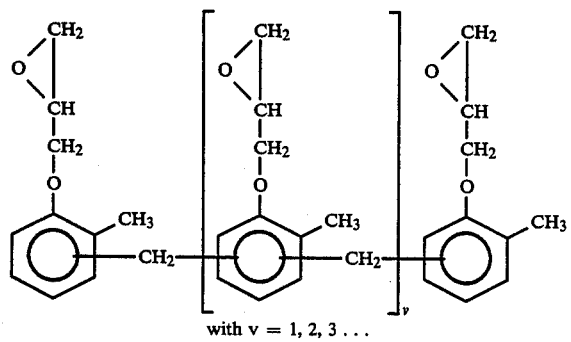

with v = 1, 2, 3 ...

90.

For the conversion to the stabilizers according to the invention, the compounds of the formula IX need not be present in the pure form, but can also be used in the form of the corresponding epoxy resins of technical-grade quality.

The novel stabilizers can be incorporated in the polymers to be stabilized without problems, and are highly suitable for stabilizing the same against light-induced oxidative degradation, i.e. their being damaged through the action of oxygen, heat and light. In addition to the excellent stabilizer activity, the novel stabilizers are also distinguished by their good compatibility with the polymers to be stabilized.

Examples of polymers which can be stabilized successfully are:

Polymers which are derived from singly or doubly unsaturated hydrocarbons, for example polyolefins such as polyethylene, which may be crosslinked, polypropylene, polybut-1-ene, polyisobutene, polymethylbut-1-ene, polymethylpent-1-ene, polyisoprene, polybutadiene, polystyrene, copolymers of the monomers underlying the homopolymers mentioned, such as ethylene-propylene copolymers, propylene-but-1-ene copolymers, propylene-isobutene copolymers, styrene-butadiene copolymers and also terpolymers of ethylene and propylene with a diene, such as, for example hexadiene, dicyclopentadiene or ethylidenenorbornene; mixtures of the abovementioned homopolymers, such as, for example mixtures of polypropylene and polyethylene, polypropylene and polybut-1-ene, polypropylene and polyisobutene or of butadiene-acrylonitrile copolymers with a styrene-butadiene copolymer.

Halogen-containing vinyl polymers, such as polyvinyl chloride, polyvinylidene chloride, polyvinyl fluoride, polychloroprene, chloro rubbers and also copolymers of vinyl chloride and vinylidene chloride with each other and with other olefinically unsaturated monomers.

Polymers which are derived from α,β-unsaturated acids and derivatives thereof, such as polyacrylates and polymethacrylates, polyacrylamides and polyacrylonitrile and also copolymers thereof with one another and with other vinyl compounds, such as acrylonitrile-butadiene-styrene, acrylonitrile-styrene and acrylonitrile-styrene-acrylate copolymers.

Polymers which are derived from unsaturated alcohols and amines and their acrylic derivatives or acetals, such as polyvinyl alcohol, polyvinyl acetate, stearate, benzoate, maleate, polyvinyl butyral, polyallyl phthalate, polyallylmelamine and copolymers thereof with other vinyl compounds, such as ethylene-vinyl compounds, such as ethylene/vinyl acetate copolymers. Homopolymers and copolymers which are derived from epoxies, such as polyethylene oxide, or the polymers which are derived from bisglycidyl ethers.

Polyacetals, such as polyoxymethylene and polyoxyethylene and also those polyoximethylenes which contain ethylene oxide as a comonomer.

Polyurethanes and polyureas

Polycarbonate

Polyamides and copolyamides which are derived from diamines and dicarboxylic acids and/or from aminocarboxylic acids or the corresponding lactams, such as nylon 6, nylon 6/6, nylon 6/10, nylon 11, nylon 12.

Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate.

Crosslinked polymers which are derived from aldehydes on the one hand the phenols, ureas and melamines on the other, such as phenol-formaldehyde, urea-formaldehyde and melamine-formaldehyde resins.

The novel compounds can finally also be used as stabilizers in the resin and surface coatings sector. Examples are thermoset and thermoplastic acrylic resins which are used for automotive coatings, acrylic resin finishes, i.e. the customary baking finishes and also very particularly mixtures based on hot-crosslinkable acrylic resin and styrene and also surface finishes and coatings based on acrylic-melamine resin and alkyd/acrylic/-melamine resin. Such surface coatings can contain as further additives other customary light stabilizers, phenolic antioxidants, pigments, dyes, metal deactivators, etc.

Of particular importance is the stabilization of polyolefins, styrene polymers, polyamides, poly(meth)acrylates and polyurethanes, for which the compounds are particularly suitable. Examples thereof are polyethylene of high and low density, polypropylene, ethylene-propylene copolymers, polystyrene, styrene-butadieneacrylonitrile terpolymers, mixtures of polyolefins or of styrene polymers and also polyurethanes based on polyethers or polyesters.

The novel stabilizers are incorporated in the polymer compositions by generally customary methods. The incorporation can be effected for example by mixing the compounds and, if desired, further additives into the melt by the methods customary in the art, before or during shaping, or alternatively by applying the dissolved or dispersed compounds to the polymer directly or mixing into a solution, suspension or emulsion thereof, if desired with subsequent evaporation of the solvent. The amounts are 0.01 to 5, preferably 0.05 to 2.5 and in particular 0.1 to 1.0, % by weight, based on the material to be stabilized. The novel compounds can also be added to the plastics to be stabilized in the form of a master batch which contains these compounds, for example, in a concentration of 1 to 50, preferably 2.5 to 20, % by weight.

The plastics stabilized by the addition of the substances according to the invention can if desired also contain other known customary additives, such as, for example, antioxidants based on phenols or sulfides, metal deactivators and light stabilizers, phosphite stabilizers, metal compounds, epoxy stabilizers and polyhydric alcohols.

Examples of antioxidants are sterically hindered phenols such as 2,6-di-tert.-butyl-4-methylphenol, 4,4'-butylidene-bis-(2,6-di-tert.-butylphenol), 4,4'-thio-bis-(2-tert.-butyl-5-methylphenol), 2,5-di-tert.-butyl-4-hydroxyanisole, dioctadecyl 2,2-bis-(3,5-di-tert.-butyl)-2-hydroxybenzyl)-malonate, 1,3,5-tris-(3,5-di-tert.-butyl-4-hydroxybenzyl)-2,4,6-trimethylbenzene, 2,4,6-tri-(3,5-di-tert.-butyl-4-hydroxybenzyl)-phenol, phenolic triazine compound such as 1,3,5-tris-(3,5-di-tert.-butyl-4-hydroxybenzyl)isocyanurate, amides or esters of β-(3,5-di-tert.-butyl-4-hydroxyphenyl)-propionic acid with, for example, octadecanol, 1,6-hexanediol, 2,2'-thiodiethylene glycol, pentaerythritol and trishydroxyethyl isocyanurate, hexamethylenediamine, esters of 3,3-bis(3-tert.-butyl-4-hydroxyphenyl)-butanoic acids with, for example, ethylene glycol, thiodipropionic acid esters with fatty alcohols, calcium or nickel salts of ethyl 3,5-di-tert.-butyl-4-hydroxybenzylphosphonate, dioctadecyl sulfide and disulfide.

Examples of metal deactivators are N,N'-diphenyloxamide, N-salicylal-N'-salicyloylhydrazine, N,N'-bis-salicyloylhydrazine, N,N'-bis-(5,5-di-tert.-butyl-4-hydroxyphenylpropionyl)-hydrazine, 3-salicyloylamino-1,2,4-triazole, bis-benzylideneoxalyldihydrazide, tris[2-tert.-butyl-4-thio(2'-methyl-4'-hydroxy-5'-tert.-butyl)phenyl-5-methylphenyl]phosphite, 2,2'-oxamido-bis[ethyl 3-(3,5-di-tert.-butyl-4-hydroxyphenyl)propionate].

The UV absorbers and light stabilizers include 2-(2'-hydroxyphenyl)-benzotriazoles such as, for example, the 5-chloro-3',5'-di-tert.-butyl and 5-chloro-3',5'-di-tert.-amyl derivative, 2-hydroxybenzophenones such as, for example, the 4-heptoxy, 4-octoxy or 4-dodecyloxy derivative, salicylates such as octylphenyl salicylate, nickel complexes such as, for example the complex with 2,2'-thio-bis-4-(1,1,3,3-tetramethylbutyl)-phenol and butylamine or other amines, or with 2-hydroxy-4-octoxybenzophenone, with dialkyldithiocarbamic acids or dialkyldithiophosphonic acids, oxamides and sterically hindered amines, for example bis(2,2,6,6-tetramethyl-4-piperidinyl)sebacate, polyesters of succinic acid with N-(2-hydroxyethyl)2,2,6,6-tetramethyl-4-hydroxypiperidine, N,N'-bis(2,2,6,6-tetramethyl-4-piperidinyl)hexamethylenediamine, 2,2,4,4-tetramethyl-7-oxa-3,20-diaza-21-oxo-dispiro-[5.1.11.2]-heneicosane, 1,1'-(1,2-ethandiyl)bis-(3,3,5,5-tetramethylpiperazinone), condensation product of N,N'-bis-(2,2,6,6-tetramethyl-4-piperidyl)hexamethylenediamine with dibromoethane or with 4-tert.-octylamino-2,6-dichloro-1,3,5-triazine or with 4-(N-morpholinyl)-2,6-dichloro-1,3,5-triazine, tetrakis-(2,2-tetramethyl-4-piperidyl)-1,2,3,4-butanetetracarboxylic acid.

Suitable phosphites are aliphatic, aromatic or aliphaticaromatic ones such as, for example, trisnonylphenyl phosphite, tris-(2,4-di-tert.-butylphenyl)phosphite, tris(2-tert.-butylphenyl)phosphite or even esters of pentaerythritol phosphite.

Examples of metal compounds known for use as stabilizers are: calcium, barium, strontium, zinc, cadmium, magnesium, aluminum and lead soaps of aliphatic carboxylic acids or oxycarboxylic acids having about 12 to 32 carbon atoms, salts of said metals with aromatic carboxylic acids such as benzoates or salicylates and also (alkyl)phenolates of these metals, furthermore organotin compounds, such as, for example, dialkyltin thioglycolates and carboxylates, and also metal oxides, for example oxides of calcium, magnesium, zinc, aluminum or of silicon.

Known epoxy stabilizers are for example epoxidized higher fatty acids such as epoxidized soyabean oil, tall oil, linseed oil or epoxidized butyl oleate and also epoxides of long-chain olefins and polyether epoxies.

Polyhydric alcohols can be for example pentaerythritol, trimethylolpropane, sorbitol or mannitol, i.e. preferably alcohols having 5 or 6 carbon atoms and 2 to 6 OH groups.

An effective stabilizer combination for poly-α-olefins, such as, for example, high, medium and low pressure polymers of $C_2$- to $C_4$-α-olefins, in particular polyethylene and polypropylene or of copolymers of such α-olefins, comprises, based on 100 parts by weight of polymer, for example 0.01 to 5 parts by weight of one of the compounds to be used according to the invention, 0.05 to 5 parts by weight of phenolic stabilizer, if desired 0.01 to 5 parts by weight of a sulfur-containing costabilizer and also if desired 0.01 to 3 parts by weight of a basic or neutral metal soap, such as, for example, calcium stearate or zinc stearate or of the corresponding oxides, if desired 0.01 to 5 parts by weight of a phosphite or phosphonite stabilizer and also if desired 0.01 to 5 parts by weight of a known UV stabilizer from the group of the alkoxyhydroxybenzophenones, 4-hydroxyphenylbenzotriazoles, benzylidenemalomononitrile esters or of so-called quenchers, such as, for example, nickel chelates. Other customary additives are for example plasticizers, lubricants, emulsifiers, fillers, such as, for example, chalk, talc, asbestos, pigments, optical brighteners, flame retardants and antistats.

The plastics stabilized according to the invention can be used in a very wide variety of forms, for example as films, fibers, ribbons, profiles or as binders for paints, adhesives or putties.

The invention is explained in more detail by the examples below.

EXAMPLE 1

A 1-liter stirred apparatus equipped with reflux condenser, internal thermometer and dropping funnel was charged with 72.8 g (0.02 mol) of compound 30 in 300 ml of toluene, and 1 g of triethylbenzylammonium chloride, 18.0 g (0.23 mol) of 50% strength sodium hydroxide solution and 77.2 g (0.40 epoxy equivalent) of a technical-grade bisphenol-A epoxide (compound 82) were added. The reaction mixture was heated to 90° C. and vigorously stirred at that temperature for 4 h. After the reaction was completed the mixture was extracted 3 times with 150 ml of water each time, the organic phase was dried over sodium sulfate, and after filtration the toluene was distilled off. The residue was then heated to 200° C. at about 1 Torr for 4 h. This gave 139.5 g of a very hard glassy solid having a softening point >250° C. and an average molecular weight >5000.

EXAMPLE 2

The intermediate was prepared as described in Example 1, but was then heated to 150° C. for 4 h. The resulting brittle, glassy product had a softening point of 220° C. and an average molecular weight of about 5000.

EXAMPLE 3

Example 2 was repeated, except that the intermediate was heated for only 2 h. The resulting brittle, glassy product had a softening point of 175° C. and an average molecular weight of 3300.

EXAMPLE 4

According to Example 1 72.8 g (0.2 mol) of compound 30 were reacted with 57.9 g (0.30 epoxy equivalent) of a technical-grade epoxide based on bisphenol-A (compound 82). The intermediate was heated to 180° C. at about 1 Torr for 4 h. This gave 120.5 g of an almost colorless, brittle glassy product having a softening point of 168° C. and an average molecular weight of 3000.

EXAMPLE 5

Example 4 was repeated, except that only 54.0 g (0.28 epoxy equivalent) of the bisphenol-A epoxide were used. The brittle, amorphous product (122.4 g) had a softening point of about 150° C. and a average molecular weight of 2800.

EXAMPLE 6

According to Example 1 36.4 g (0.1. mol) of compound 30 in 150 ml of toluene were reacted with 23.2 g (0.12 epoxy equivalent) of a technical-grade bisphenol-A epoxide (compound 82) in the presence of 0.5 g of triethylbenzylammonium chloride and 9.0 g (0.11 mol) of 50% strength sodium hydroxide solution. The intermediate was then heated to 180° C. at about 1 Torr for 4 h. This gave 56.3 g of a colorless, amorphous solid having a softening point of 135° C. and an average molecular weight of 1960.

EXAMPLE 7

Example 4 was repeated, except that 56.0 g (0.2 mol) of compound 29 instead of compound 30 were used. This gave 105.3 g of a colorless product having a softening point >250° C. and a molecular weight of 6800.

EXAMPLE 8

Example 1 was repeated, except that instead of compound 30 28.0 g (0.1 mol) of compound 29 were reacted with 27.0 g (0.14 epoxy equivalent) of a technical-grade bisphenol-A epoxide (compound 82). The intermediate was heated to 180° C. at about 1 Torr for 4 h. This gave 53.7 g of a colorless product having a softening point of 147° C. and an average molecular weight of 2400.

EXAMPLE 9

Example 6 was repeated, except that instead of compound 30 28.0 g (0.1 mol) of compound 29 were reacted, affording 50.5 g of a colorless, amorphous product having a softening point of 130° C. and an average molecular weight of 1640.

EXAMPLE 10

Example 4 was repeated, except that instead of compound 30 48.0 g (0.2 mol) of compound 31 were reacted, affording 97.8 g of a colorless amorphous product having a softening point of 145° C. and an average molecular weight of 2580.

EXAMPLE 11

A 1-liter stirred apparatus equipped with internal thermometer, reflux condenser and dropping funnel was charged with 100 ml of toluene, followed by 24.0 g (0.1 mol) of compound 43 (educt I), 0.3 g of triethylbenzylammonium chloride, 9.0 g (0.11 mol) of 50% strength sodium hydroxide solution and 38.6 g (0.20 epoxy equivalent) of a technical-grade bisphenol-A epoxide (compound 82; educt II), and the mixture was heated to 90° C. and stirred for 4 h. It was then extracted 3 times with 50 ml of water each time, the organic phase was dried with sodium sulfate, and after filtration the toluene was distilled off. The intermediate thus obtained was heated to 180° C. at about 1 Torr for 4 h. This gave 82.3 g of a colorless, very hard product having a softening point >250° C.

EXAMPLES 12 to 15

Carried out in accordance with Example 11.

| Example | Educt I g/mol | | Educt II g/epoxy equivalent | | g | Product softening point (°C.) | M |
| --- | --- | --- | --- | --- | --- | --- | --- |
| 12 | 24.0 | 0.1 | 34.8 | 0.18 | 50.3 | 235 | 6340 |
| 13 | " | " | 30.9 | 0.16 | 47.3 | 150 | 3730 |
| 14 | " | " | 27.1 | 0.14 | 45.2 | 132 | 1820 |
| 15 | " | " | 23.2 | 0.12 | 42.6 | 125 | 1330 |

EXAMPLES 16 TO 18

Example 11 was repeated, using instead of compound 43 27.7 g (0.1 mol) of compound 72 as educt I and also 17.6 g (0.22 mol) of 50% strength sodium hydroxide solution.

| Example | Educt I g/mol | | Educt II g/epoxy equivalent | | g | Product softening point (°C.) | M |
| --- | --- | --- | --- | --- | --- | --- | --- |
| 16 | 27.7 | 0.1 | 26.9 | 0.14 | 48.9 | 137 | 2200 |
| 17 | " | " | 29.3 | 0.15 | 50.7 | 145 | 3300 |
| 18 | " | " | 31.2 | 0.16 | 52.5 | 156 | 5000 |

EXAMPLE 19

Carried out like Example 16, except that here no triethylbenzylammonium chloride was added. 46.0 g of an amorphous product having a softening of 138° C. and an average molecular weight of 2100 were obtained.

EXAMPLE 20

Example 19 was repeated, except that the educts were reacted with one another under reflux, affording 47.3 g of an amorphous product having a softening point of 139° C. and an average molecular weight of 2400.

EXAMPLE 21

A 1-liter stirred flask equipped with internal thermometer and reflux condenser was charged with 200 ml of toluene, followed by 55.3 g (0.2 mol) of compound 72 (educt I), 0.6 g of benzyltriethylammonium chloride and 19.8 g of KOH powder, and the batch was heated up to 90° C. 52.5 g (0.30 epoxy equivalent) of a technical-grade bisphenol-F epoxide (compound 81, educt II) were then added, and the batch was stirred at 90° C. for a further 2 h. This was followed by two pressure filtrations, removal of the toluene by distillation and heating of the resulting intermediate to 180° C. at 30 Torr for 3 h. This gave 97.3 g of an amorphous, almost colorless product having a softening point of 125° C. and an average molecular weight of 2300.

EXAMPLE 22

According to Example 21 55.3 g (0.2 mol) of compound 72 (educt I) were reacted with 37.5 g (0.30 epoxy equivalent) of a technical-grade butanedioldiglycidyl ether (compound 77; educt II), affording 79.8 g of a colorless, amorphous product having a softening point of 59° C. and an average molecular weight of 1720.

EXAMPLE 23

A 500-ml stirred apparatus equipped with reflux condenser and internal thermometer was charged with 200 ml of toluene, 55.3 g (0.2 mol) of compound 72, 19.8 g of KOH powder and 53.8 g (0.28 epoxy equivalent) of a technical-grade bisphenol-A epoxide (compound 82), and the mixture was heated to 90° C., stirred for 1 hour, pressure-filtered twice and the toluene was distilled off. The intermediate thus obtained was heated to 180° C. at 30 Torr for 3 h. This gave 96.6 g of a colorless, amorphous product having a softening point of 132° C. and an average molecular weight of 2200.

EXAMPLE 24

This example shows the volatility of the stabilizers according to the invention compared with stabilizers of German Patent No. 2,606,026 and German Offenlegungsschrift No. 2,634,957.

The volatilities were determined in an apparatus for thermogravimetric analysis. Equal amounts (500 mg) of the compounds according to the invention and of the comparative substances were to this end heated up in a stream of nitrogen (1 liter/min) to 300° C. at a heating-up rate of 2 K/min and the loss of substance was measured in percent by weight.

| Stabilizer of example | Loss of substance in % by weight on reaching ... °C. | | | |
| --- | --- | --- | --- | --- |
| | 200 | 260 | 300 | 10 min at 300 |
| 4 | 0 | 0.1 | 0.6 | 2.5 |
| 6 | 0.1 | 0.2 | 0.9 | 2.7 |
| 8 | 0 | 0.1 | 0.6 | 2.0 |
| 10 | 0 | 0.2 | 1.0 | 2.7 |
| 17 | 0 | 0 | 3.3 | 8.5 |
| 20 | 0 | 0.2 | 2.6 | 8.3 |
| 22 | 0.1 | 0.5 | 4.2 | 9.4 |
| Comparison A[1] | 0.8 | 2.8 | 12.3 | 29.8 |
| Comparison B[2] | 17.9 | 75 | at 280° C.: | 100% |

[1]Stabilizer of Example 31 of German Patent 2,606,026
[2]Stabilizer of Example 21 of German Offenlegungsschrift 2,634,957.

EXAMPLES 25 AND 26

EXAMPLE 25

A mixture comprising 100 parts by weight of polypropylene (MFI 230/5: 4 g/min; density at 23° C.: 0.903 g/cm³),
0.1 part by weight of bis-[3,3-bis-(4'-hydroxy-3'-tert.-butylphenyl)-butanoic acid]glycol ester,
0.1 part by weight of calcium stearate and
0.3 part by weight of the stabilizer according to the invention under test was homogenized in a laboratory high-speed mixer. This mixture was injection-molded at 240° C. in an SP 50 Windsor injection-molding machine into 60×60×1 mm sheets. These sheets were die-cut into T-shaped test specimens in accordance with DIN 53,383.

To determine the heat aging resistance, these test specimens were suspended in a circulating air drying cabinet in a motor-driven frame with rotating trays and subjected, with a constant fresh air supply, to a temperature of 140° C.

The time when in some areas incipient local embrittlement occurred, characterized according to DIN 53,383 by the formation of discolored, cloudy, partly crumbling areas, was recorded.

The results are shown in the table below:

| Stabilizer of example | Incipient embrittlement after ... days |
|---|---|
| 20 | 31 |
| Comparison A | 13 |
| Comparison C[(1)] | 5 |

[(1)]without stabilizer under test.

EXAMPLE 26

A mixture comprising
100 parts by weight of polypropylene powder (MFI 230/5: 18 g/10 min; density at 23° C.; 0.903 g/cm³);
0.1 part by weight of bis-[3,3-bis(4'-hydroxy-3'-tert.-butylphenyl)-butanoic acid]glycol ester,
0.1 part by weight of calcium stearate,
0.05 part by weight of tri-(2,4-di-tert.-butylphenyl)-phosphite and
0.3 part by weight of the stabilizer to be tested was used to prepare test specimens which were then subjected to the thermal aging stability test, both steps being carried out as in Example 25.

The results are shown in the table below:

| Stabilizer of example | Incipient embrittlement after ... days |
|---|---|
| 14 | 39 |
| 20 | 37 |
| Comparison A | 21 |
| Comparison C | 20 |
| Comparison D[(1)] | 6 |

[(1)]unstabilized polypropylene.

EXAMPLE 27

A mixture comprising
100 parts by weight of polypropylene (MFI 230/5: 4 g/10 min, density at 23° C.: 0.903 g/cm³),;
0.1 part by weight of bis-[3,3-bis-(4'-hydroxy-3'-tert.-butylphenyl)-butanoic acid]glycol ester,
0.1 part by weight of calcium stearate and
0.15 part by weight of the stabilizer to be tested was homogenized in a laboratory high-speed mixer. This stabilized mixture thus prepared was processed on a laboratory film blow molding unit (screw diameter 30 mm, length 20 D) into blow-molded films of about 100 μm in thickness. These films were die-cut into test specimens in accordance with DIN 53,455, shape 3, reduced on a scale of 1:3.

To determine the light stability, these samples were subjected in an arrangement in accordance with DIN 53,387 No. 5.1 note 2 in a ®Xenotest 450 accelerated exposure and weathering instrument (Original Hanau Quarzlampen GmbH) to irradiation with alternating light. The radiation intensity was modulated by 6 IR filters+1 UV filter. The light stability was tested in accordance with DIN 53,387 (17 min dry period, 3 min spraying with water, black panel temperature 45±5° C., relative humidity during the dry period 70 to 75%). The parameter measured was the elongation at break on a tensile tester using a take-off speed of 5 cm/min after a certain exposure time in hours.

The results are shown in the table below.

| Stabilizer of example | Exposure time to 50% value | 10% value |
|---|---|---|
| | (elongation at break relative to starting value) | |
| 14 | 700 h | 790 h |
| Comparison C | 220 h | 260 h |

EXAMPLE 28

The sheets prepared as described in Example 25 were diecut into test specimens in accordance with DIN 53,455, shape 3, reduced on a scale of 1:3.

To determine the light stability, these samples were subjected in a Xenotest 450 instrument to irradiation with permanent light. The conditions used were 6 IR filters and 1 UV filter and also a black panel temperature of about 75° C. (at the end of the dry period), 17 min dry period and 3 min spraying with water and a relative humidity during the dry period of about 70%. The parameter measured was the elongation at break on a tensile tester with a takeoff speed of 5 cm/min after certain exposure times. These data were then used to obtain the following results:

| Stabilizer of example | Exposure time to 50% value | 10% value |
|---|---|---|
| | (elongation at break relative to starting value) | |
| 20 | 1600 h | 1750 h |
| Comparison C | 100 h | 175 h |

We claim:

1. A compound of the formula (I)

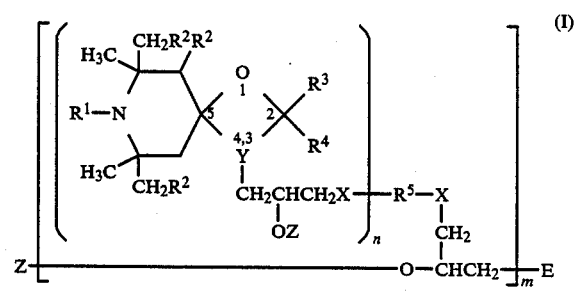

in which
n is a whole number from 1 to 4, m is a whole number from 1 to 100, $R^1$ is hydrogen, $C_1$- to $C_4$-alkyl, benzyl, allyl, $C_2$- to $C_{30}$-alkanoyl, $C_2$- to $C_{20}$-alkenoyl, $C_7$- to $C_{11}$-aroyl, $C_8$- to $C_{14}$-arylalkanoyl or $C_8$- to $C_{20;l}$-alkylaryl, $R^2$ is hydrogen or $C_1$- to $C_4$-alkyl, $R^3$ and $R^4$ are identical or different and denote hydrogen, $C_1$- to $C_{13}$-alkyl, unsubstituted or chlorine- or $C_1$- to $C_4$-alkyl-substituted phenyl, unsubstituted or $C_1$- to $C_4$-alkyl-substituted $C_7$- to $C_{14}$-aralkyl, or together with the carbon atom connecting them denote an unsubstituted or $C_1$- to $C_4$-alkyl-mono-, -di-, -tri- or -tetrasubstituted $C_5$- to $C_{12}$-cycloalkyl or piperidine ring, $R^5$ when n=1 denotes $C_2$- to $C_{18}$-alkylene, unsubstituted or $C_1$- to $C_4$-alkyl-mono- or -di substituted phenylene, $\alpha,\omega$-dicarboxyl-$C_1$- to $C_8$-alkylene, a dicarboxy-$C_6$-ring, $C_7$- to $C_{14}$-aralkylene, cycloalkylene, dicycloalkylene, tricycloalkylene, bismethylenemonocycloalkylene, bismethylenedicycloalkylene, bismethylenetricycloalkylene, arylene, bisarylenealkyl, which radicals can also be bromine- or chlorine- or $C_1$-$C_4$-alkyl-substituted, a radical

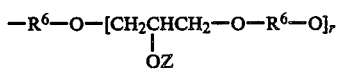

with r=1 to 20 and $R^6$ equal to $C_2$- to $C_{12}$-alkylene, cycloalkylene, dicycloalkylene, tricycloalkylene, bismethylenemonocycloalkylene, bismethylenedicycloalkylene, bismethylenetricycloalkylene, arylene, bisarylenealkyl, which radicals can also be bromine- or chlorine- or $C_1$- to $C_4$-alkyl-substituted, $R^5$ when n=2 denotes the radical of a trifunctional alcohol or amine, the trifunctional radical of an aliphatic alcohol which contains further hydroxyl groups, or the trifunctional radical of a novolak based on phenyl, cresol, bisphenol-F or bisphenol-A, $R^5$ when n=3 denotes the tetrafunctional radical of an aliphatic alcohol or amine or of a novolak based on phenol, cresol, bisphenol-F or bishenol-A or the radical

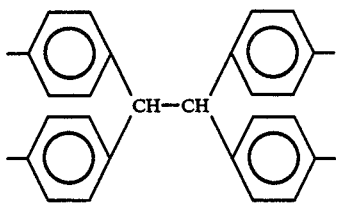

$R^5$ when n=4 denotes a pentafunctional radical of a polyol, or a polyamine or of a novolak based on phenol, cresol, bisphenol-F or bisphenol-A, Y denotes

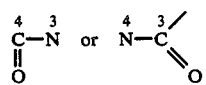

and occupies ring positions 3, 4 in the formula (I), X represents —O— or

where $R^7$ is hydrogen, $C_1$- to $C_{30}$-alkyl, a piperidine ring which is substituted by 1 to 4 $C_1$- to $C_4$-alkyl groups, or a radical of the formula (II)

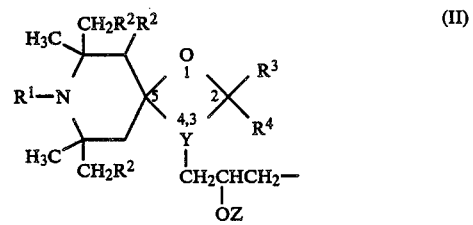

in which $R^1$, $R^2$, $R^3$, $R^4$, Y have the abovementioned meanings,

Z is hydrogen,

E stands for hydrogen, hydroxyl, a radical of the formula (IV), (V) or (VI)

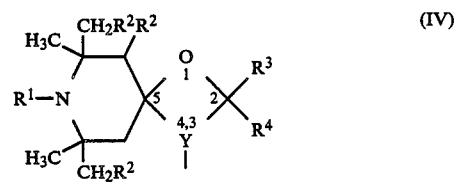

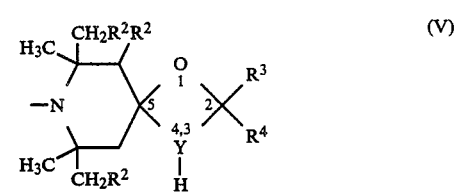

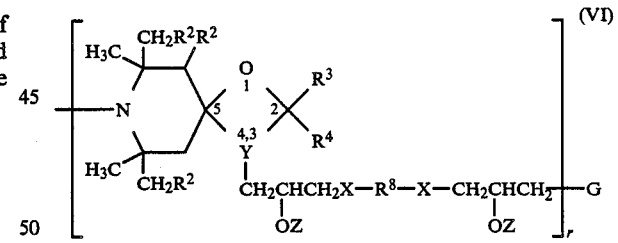

in which $R^1$, $R^2$, $R^3$, $R^4$, $R^5$, X, Y and Z have the abovementioned meanings, r represents a whole number from 1 to 100, and G is a radical of the formula (IV) or (V) and $R^8$ has the meaning of formula (VII)

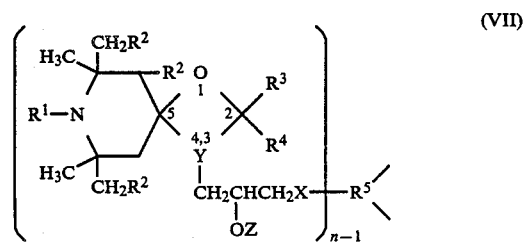

in which $R^1$, $R^2$, $R^3$, $R^4$, $R^5$, X, Y, Z and n have the abovementioned meanings.

2. A compound as claimed in claim 1, wherein n is 1 and m is a number from 2 to 20.

3. A compound as claimed in claim 2 wherein $R^1$ and $R^2$ are hydrogen.

4. A compound as claimed in claim 1, wherein $R^1$ and $R^2$ are hydrogen.

5. A process for preparing compounds of the formula (I) of claim 1, which comprises reacting diazaspirodecanes of the formula (VIIIa) or (VIIIb)

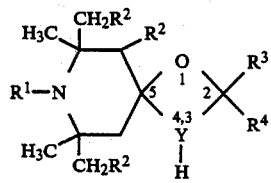

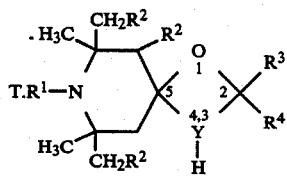

in which $R^1$, $R^2$, $R^3$, $R^4$ and Y have the abovementioned meanings and T is a nonoxidizing mineral acid or an aliphatic or aromatic sulfonic of phosphonic acid, an aliphatic mono-, di- or polycarboxylic acid or an aromatic mono- or dicarboxylic acid, and epoxides of the formula (IXa) or (IXb)

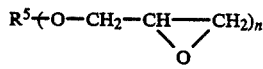

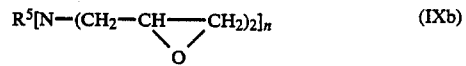

in which $R^5$ and n have the abovementioned meanings, the compounds (VIIIa) and (VIIIb) being used in an inert organic solvent in the presence of 0.2 to 1.5 times the equivalent amount of a base, relative to the compound (VIIIa), or 1.2 to 2.5 times the equivalent amount of a base in the case of using compound (VIIIb), at a temperature of 40° to 180° C. with a deficiency of one to a fifth equivalent, based on the epoxy groups in the compounds (IXa) or (IXb).

6. A process as claimed in claim 5, wherein the intermediates prepared according to said process are subsequently converted in the presence or absence of solvent into higher molecular weight compounds by heating to a temperature of from 100° to 240° C.

7. A process as claimed in claim 6, wherein a phase transfer catalyst is added, and wherein the intermediates are converted into higher molecular weight compounds by heating to a temperature of from 100° to 240° C. in the presence of catalysts.

8. A process for stabilizing synthetic polymers against the damaging influence of light, which comprises adding to the polymers, 0.01 to 5 parts by weight, based on polymer, of the stabilizer as claimed in claim 1.

9. Process according to claim 8, wherein the polymer is a polyolefin, a polyacrylate, a polymethacrylate or a homopolymer or copolymer of styrene.

10. Process according to claim 8, wherein the polymer is the solids content of a paint.

11. A process according to claim 3, wherein said stabilizer is added to the polymers in combination with conventional stabilizers.

12. A synthetic polymer stabilized against UV decomposition and containing 0.01 to 5 parts by weight, based on polymer, of a stabilizer as claimed in claim 1.

* * * * *